US006267753B1

(12) United States Patent
Kao

(10) Patent No.: US 6,267,753 B1
(45) Date of Patent: Jul. 31, 2001

(54) ROBOTIC MEDICAMENT DISPENSER

(76) Inventor: Ti Kao, P.O. Box 740014, Rego Park, NY (US) 11374-0014

( * ) Notice: Subject to any disclaimer, the term of this patent is extended or adjusted under 35 U.S.C. 154(b) by 0 days.

(21) Appl. No.: 08/892,571

(22) Filed: Jul. 15, 1997

(51) Int. Cl.[7] .................................................... A61B 19/00
(52) U.S. Cl. ............................... 604/416; 604/82; 604/87
(58) Field of Search ................................ 604/82, 83, 84, 604/85, 87, 89, 403, 408, 405, 406, 410, 416, 903; 221/63, 91, 2; 206/219, 220, 221

(56) References Cited

U.S. PATENT DOCUMENTS

| | | | |
|---|---|---|---|
| 3,502,244 | 3/1970 | Irvin | 221/63 |
| 4,128,188 | 12/1978 | White | 221/91 |
| 4,175,558 | 11/1979 | Hess, III et al. | 128/214 |
| 4,340,152 | 7/1982 | Ekholm, Jr. | 222/1 |
| 4,540,403 | 9/1985 | Theeuwes | 604/85 |
| 4,785,969 | 11/1988 | McLaughlin | 221/2 |
| 4,863,454 * | 9/1989 | LeBove | 604/416 |
| 4,906,103 | 3/1990 | Kao | 366/130 |
| 4,980,292 | 12/1990 | Elbert et al. | 435/289 |
| 5,014,875 | 5/1991 | McLaughlin et al. | 221/2 |
| 5,181,189 | 1/1993 | Hafner | 368/10 |
| 5,190,185 | 3/1993 | Blechl | 221/1 |
| 5,196,001 | 3/1993 | Kao | 604/416 |
| 5,208,762 | 5/1993 | Charhut et al. | 364/478 |
| 5,263,929 * | 11/1993 | Falcone et al. | 604/416 X |
| 5,278,149 | 1/1994 | Provost et al. | 514/23 |
| 5,329,459 | 7/1994 | Kaufman et al. | 364/479 |
| 5,348,061 | 9/1994 | Riley et al. | 141/104 |
| 5,377,864 | 1/1995 | Blechl et al. | 221/2 |
| 5,460,294 | 10/1995 | Williams | 221/2 |
| 5,494,196 | 2/1996 | Tyner | 222/147 |
| 5,502,944 | 4/1996 | Kraft et al. | 53/55 |
| 5,511,594 | 4/1996 | Brennan et al. | 141/98 |

* cited by examiner

*Primary Examiner*—Ronald Stright, Jr.
(74) *Attorney, Agent, or Firm*—Lathrop & Clark LLP

(57) ABSTRACT

Robotic manipulation of three-part plastic preparation assemblies automatically produces IV solutions which conform to a input specifications of a pharmacist located on site or remotely, including preparation telerobotically. The transparent plastic bag assemblies are stored in a magazine, and are extracted automatically one by one for preparation of individual prescriptions. A supply bag is prefilled with U.S.P. water and is connected through a valve to a mixing bag. Unit dose holders with medicaments and pH adjusting chemistries are dispensed into the mixing bag through an inlet where they are broken open by manipulation, and water is introduced. The bag contents are mixed by rotation of a magnetic mixing bar. The mixing bag is connected by a second valve through a filter to an administration bag. Negative pressure is applied to the administration bag to draw the solution through the filter. The administration bag is then heat sealed and severed from the filter for delivery to the patient. For ophthalmic solutions, a plurality of precapped containers are formed on the administration bag, and liquid from the administration bag is drawn into the individual ophthalmic solution containers, which are then heat sealed and severed from the administration bag.

12 Claims, 4 Drawing Sheets

ROBOTIC MEDICAMENT DISPENSER

FIELD OF THE INVENTION

The present invention relates to automated dispensing apparatus in general, and to machines for preparing pharmaceutical solutions for intravenous injection and ophthalmic application in particular.

BACKGROUND OF THE INVENTION

Typically, bags of solutions for intravenous injection of patients are prepared manually by pharmacists or pharmacist's aides. Each solution must be tailored to the particular need of the patient with respect to composition, quantity and type of medicament, and pH level. Variations from required levels can have deleterious, even fatal, consequences for the patient. Pharmacists and their assistants are highly trained and conscientious professionals. Nonetheless, under the pressures of time and environment, these professionals can make errors. In addition, the need to keep the final preparation sterile requires costly and time-consuming measures on the part of those who prepare the solutions.

Heat sterilization of solutions for intravenous injection, for example as part of a total parenteral nutrition system can lead to carmelization of the injectable sugars, which can have enormously negative consequences for the health of the patient. In my prior U.S. Pat. No. 4,906,103 I disclosed a system for the cold sterilization of solutions which completely avoids the hazards of heat sterilization. In my prior U.S. Pat. No. 5,196,001 I disclosed a preparation assembly and unit dose medicament containers for use in a cold sterilization system which permitted controlled pre-preparation dosing of medicaments.

Great strides have been made in automatic dispensing of solid pills and powders by way of computer controlled robotic assemblies. With greater attention to costs at all levels of the health care system, efforts have been made to limit the direct intervention of doctors and pharmacists in dispensing of medications, while at the same time maintaining adequate control by these professionals. Solid pills and capsules are by their nature suited to dispensing in unit doses, but the remotely operated drawers and dispensers which are adequate for pills are not effective for the preparation of individualized injectable solutions. Furthermore, robotic devices for dispensing liquids from a storage vessel of liquid present serious concerns in the preparation of solutions for administration to humans. Typically an aliquot of liquid would be dispensed by a micropump. Yet pumps are subject to malfunctions, and great care needs to be taken to quality check whether the desired quantity of liquid has actually been dispensed. In any event, no physical record remains to verify the amount and type of liquid dispensed. What is needed is a consistent and effective apparatus for preparing and dispensing liquid medicament solutions.

SUMMARY OF THE INVENTION

The apparatus of this invention employs robotic manipulation of three-part plastic preparation assemblies to automatically produce IV solutions which conform to the pharmacist's input specifications. The assemblies are stored in a magazine, and are extracted automatically one by one for preparation of individual prescriptions. A supply bag is prefilled with U.S.P. water and is connected through a valve to a transparent plastic mixing bag. Unit dose holders containing various medicaments and pH adjusting chemistries are dispensed into the mixing bag through an inlet. The unit dose holders are broken open by manipulation of the bag, and the U.S.P. water is introduced into the bag through the inlet. The contents of the unit dose holders and the water is mixed within the mixing bag by rotation of a magnetic mixing bar. The mixing bag is connected by a second valve through a filter to an administration bag. Negative pressure is applied to the administration bag to draw the solution through the filter. The administration bag is then heat sealed and severed from the filter for delivery to the patient. For ophthalmic solutions, a plurality of pre-capped containers are formed on the administration bag, and liquid from the administration bag is drawn into the individual ophthalmic solution containers, which are then heat sealed and severed from the administration bag.

The assembly of this invention is well suited to remote preparation of solutions, or to automated preparation of solutions, both under the supervision of a pharmacist. Furthermore, the exhausted mixing bag for each prepared solution may be stored, or an image of it may be stored, for later analysis of a particular solution should questions arise about its content after it has been administered to a patient. The assembly may be used for telerobotic preparation of solutions aboard spacecraft, where a licensed pharmacist will usually not be on site.

It is an object of the present invention to provide an apparatus for formulating solutions for intravenous injections without significant human intervention.

It is an additional object of the present invention to provide an apparatus for automatically and reliably preparing intravenous solutions.

It is another object of the present invention to provide a injectable solution system which displays visual markers to validate the prescribed contents of the solution.

It is a further object of the present invention to provide an apparatus for preparing human injectable solutions which may be operated in space by an earthbound pharmacist.

It is a still further object of the present invention to provide an apparatus for automatically preparing solutions for ophthalmic application.

Further objects, features and advantages of the invention will be apparent from the following detailed description when taken in conjunction with the accompanying drawings.

DESCRIPTION OF THE PREFERRED EMBODIMENTS

Figure 1:
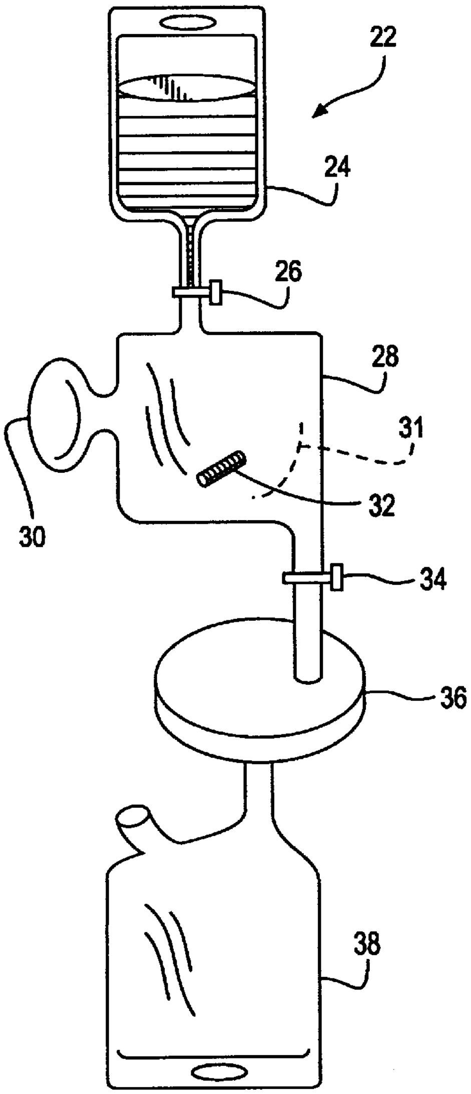
FIG. 1 is a schematic view of a preparation assembly for use within the robotic apparatus of this invention.

Referring more particularly to FIGS. 1–8, wherein like numbers refer to similar parts, the robotic solution preparation apparatus 20 of this invention employs preformed preparation assemblies 22 which are stored in a magazine for immediate access by the mechanism 20. Each preparation assembly has three connected bags in which the solution is prepared and contained. A transparent plastic supply bag 24, as shown in FIG. 1, is prefilled and stored with U.S.P. water. The supply bag 24 is connected through a first valve 26 to a mixing bag 28. The mixing bag is also transparent plastic and has an inlet 30 through which unit dose containers are introduced into a mixing chamber 31. A magnetic mixing bar 32 is disposed within the mixing bag, or may be added in the mixing step. The mixing bag 28 is connected by a second valve 34 through a filter 36 to an administration bag 38.

Figure 2:
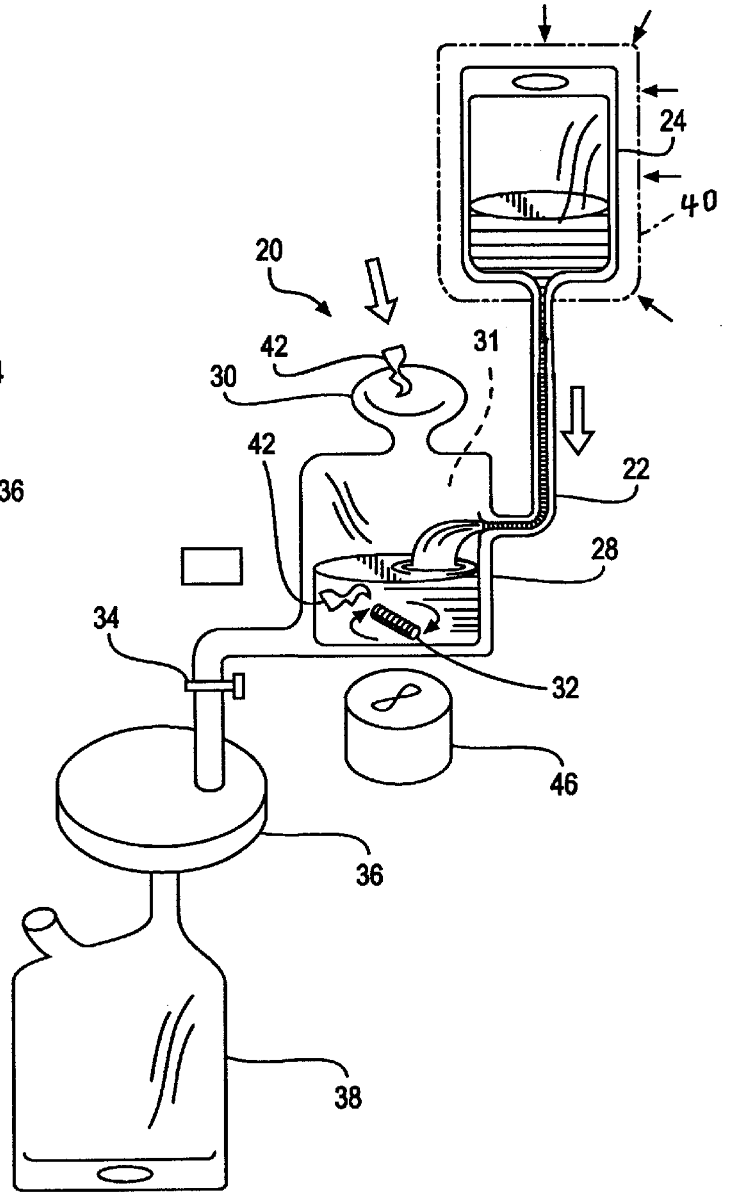
FIG. 2 is a schematic view of the assembly of FIG. 1 engaged within the robotic apparatus and showing the addition of prepared unit doses of medicaments and chemicals.

When it is desired to prepare a solution for intravenous administration, the pharmacist enters the required prescription into the computer controller. The controller then causes a preparation assembly 22 to be accessed from the magazine. In a preferred embodiment the controller will control the mechanisms associated with the apparatus without human intervention until the completion of the final container of solution for administration to a patient. The apparatus has a means for supporting and advancing the assembly 22 from the magazine which may be any conventional conveyor apparatus. The preparation assembly 22 is advanced so as to enclose the supply bag 24 in a positive pressure chamber 40, as shown in FIG. 2. While the supply bag 24 is subjected to positive pressure to force U.S.P. water from the supply bag 24 through the first valve 26, the mixing bag 28 is positioned with its inlet 30 opening upwardly such that unit dose holders 42 may be deposited into the mixing chamber 31. Because the unit dose holders are solid, easily manipulated objects, unit dose holders for a variety of medicaments may be stored in an automatically accessible rack or magazine for selection by the apparatus 20. When the mixing bag inlet 30 is in position, the controller directs that the proper number and type of unit dose holder 42 are introduced into the mixing chamber 31. The unit dose holders 42 contain premeasured quantities of medicaments and pH adjusting chemistries.

As the unit dose holders are introduced into the mixing chamber 31, they are broken to allow the powders or concentrated liquids contained therein to escape and mingle with the U.S.P. water contained in the mixing chamber 31. The unit dose holders 42 may be broken by several means. For example, the dose holders my be broken by a mechanism which ruptures them as they are dropped into the mixing bag so both the medicament contents and the empty holders enter the mixing bag, or they may be broken by a mechanism which massages the mixing bag after they have been introduced. In any event, both the contents of the unit dose holder and the unit dose holder itself are delivered into the mixing bag. The contents are mixed by a magnetic bar stirrer 46 positioned beneath the mixing bar 32 which causes the mixing bar to rotate and to thereby thoroughly mix the contents. The unit dose holders 42 may be of the type disclosed in my U.S. Pat. Nos. 4,906,103 and 5,196,001, the disclosures of which are incorporated by reference herein, or of the type shown in FIGS. 6–8. An electric eye 44 is positioned to detect the level of the contents within the mixing chamber 31. When the proper level is reached, the pressure on the supply bag 24 is halted.

Figure 3:
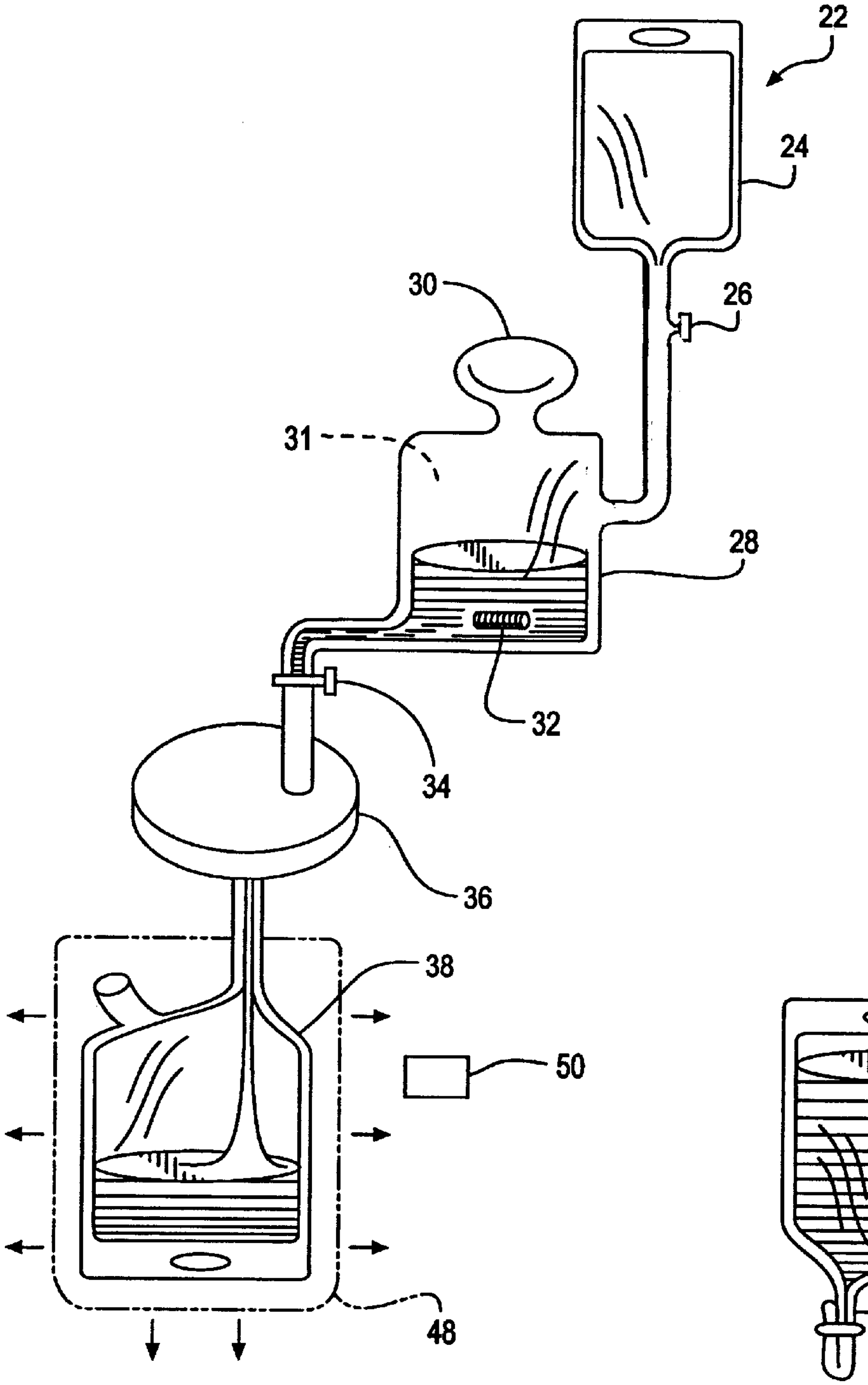
FIG. 3 is a schematic view of the assembly of FIG. 2 within the robotic apparatus with the administration bag being subjected to reverse pressure to draw the solution through a filter.
Figure 4:
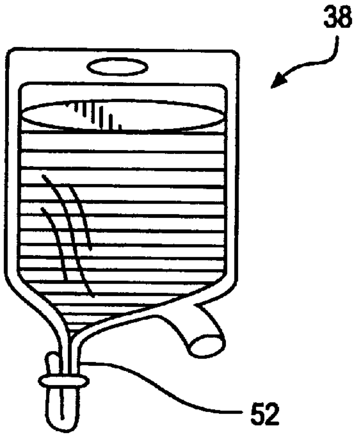
FIG. 4 is a schematic view of the final dispensed administration bag containing a sterile solution ready for patient administration.

As shown in FIG. 3, after mixing, the second valve 34 is opened and the administration bag is placed in a negative pressure chamber 48, where negative pressure is drawn to cause the liquid to pass through the filter 36 into the administration bag. An electric eye 50 is positioned to determine the level and specific density of the liquid within the administration bag 38, and to halt the application of negative pressure when desired levels are reached. The filter 36 sterilizes the solution without requiring it to be subjected to elevated temperatures.

The apparatus 20 then severs the administration bag 38 from the preparation assembly 22, and seals the end 52 such as by heat sealing. The administration bag 38 is then dispensed from the apparatus 20 for delivery to the patient and intravenous administration. It should be noted that the apparatus 20 may be constructed using conventional conveyance mechanisms, and that the assemblies 22 may be constructed with protruding engagement openings or position markers to assist in precise placement and manipulation of the assemblies by robotic elements.

Figure 6:
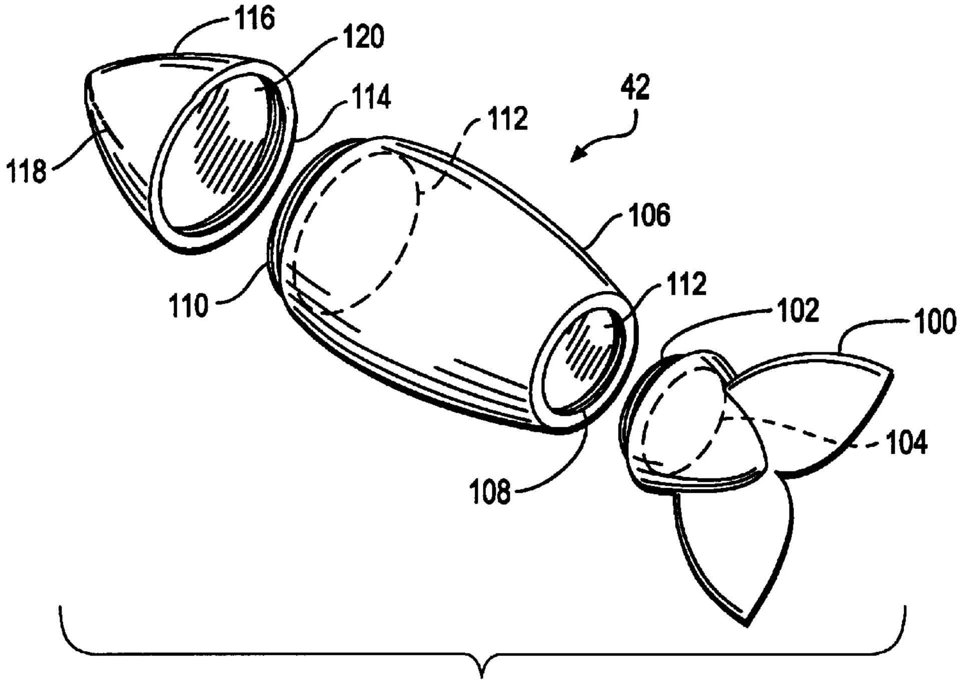
FIG. 6 is an exploded isometric view of a unit dose holder for use within the assembly of FIG. 1.
Figure 7:
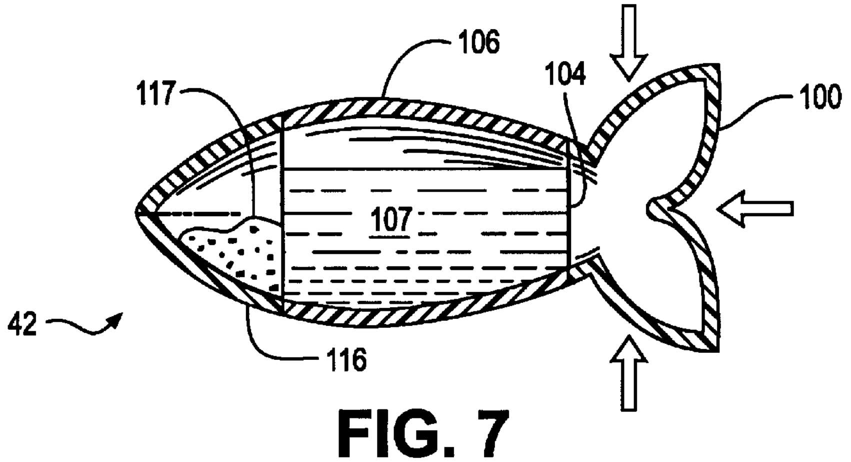
FIG. 7 is a cross-sectional view of the unit dose holder of FIG. 6, showing the location of pressure application.
Figure 8:
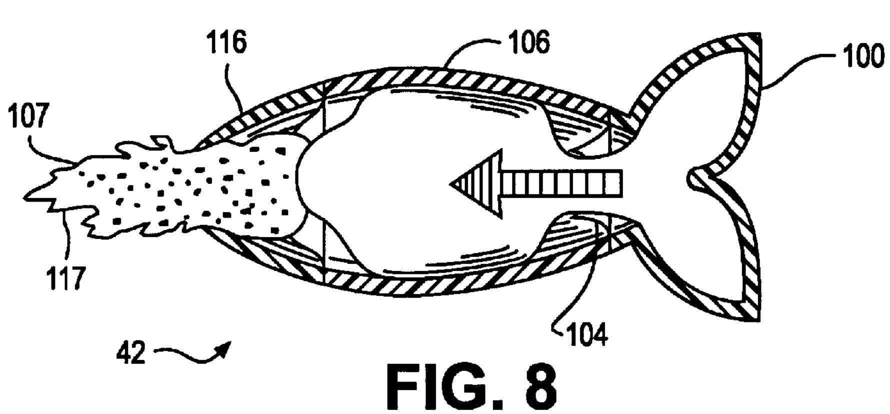
FIG. 8 is a cross-sectional view of the unit dose holder of FIG. 7 with its contents being expelled in response to the applied pressure.

An example of a unit dose holder 42 particularly suited to automatic rupture by the robotic apparatus of this invention is shown in FIGS. 6–8. The unit dose holder 42 is formed of three plastic parts. To readily convey the function of the unit dose holder, it may be formed to simulate a fish. The unit dose holder 42 has a pressurized gas container 100 corresponding in position to the fish's tail. The gas container 100 has a male threaded outlet 102 which is sealed with a readily ruptured membrane 104. The gas container 100 is formed of resilient plastic and is filled with pressurized, sterilized, and filtered air. The outlet 102 of the gas container 100 is threaded into engagement with a central medicament container 106 which corresponds in position to the fish's body. The central container 106 has a female threaded inlet 108 and a male threaded outlet 110, each of which are sealed with readily ruptured membranes 112. The central container 106 is filled with concentrated medicinal solutions 107 and is threadedly engaged with the female threaded inlet 114 of a discharge container 116. The discharge container 116 corresponds in position to the head of the fish. The discharge container 116 may be filled with medicinal powder 117, and has a weakened line of plastic 118 which corresponds in position to the fish's mouth. The weakened line of plastic 118 is easily ruptured in response to internal pressure within the unit dose holder. The threaded inlet of the discharge container is sealed with a readily ruptured membrane 120. When pressure is applied externally to the gas container 100, as shown in FIG. 7, the membranes 104, 112 are ruptured, and the gas enters the central container 106, applying pressure to the contents which in turns ruptures the membranes 120, 112 between the central container 106 and the discharge container 116. The result is to burst the line of weakened plastic 118 and expel the entire liquid and powder contents of the unit dose holder out from the unit dose holder, as shown in FIG. 8.

The robotic apparatus 20 thus fully controls the preparation of the administration bag without requiring manual processing. Not only can the apparatus thus rapidly make the necessary formulations, but it can be done with unwavering procedures which are not subject to human error. Furthermore, by the use of prefilled unit dose holders, variables with respect to precise quantities of liquids can be eliminated. A single pharmacist may thus oversee a large quantity of preparations. Moreover, because of the automatic nature of the apparatus 20, the pharmacist may be located remotely from the actual preparation site. For remote operation, the apparatus is outfitted with a radio receiver for receiving analog or digital signals, and a controller for receiving the signals and carrying out operations in response to those signals. This ability to remotely prepare solutions is particularly advantageous when it is costly or dangerous to have the pharmacist in close proximity to the patient. For example, a robotic apparatus 20 may be positioned on an orbiting space station, with the pharmacist operating the machine from earth. Or, as another example, a robotic apparatus in a combat field hospital may be operated by a pharmacist at the rear.

The mixing chamber also provides a valuable supervisory function, in that the exhausted unit dose holders may be preserved along with the used mixing chamber for several days after the final solution has been administered to the patient. Should any untoward symptoms develop in the patient, an accurate and verifiable record of the actual medicaments administered may be obtained by retrieving the mixing chambers used in the preparation of solutions for that particular patient, and examining the exhausted unit dose holders therein. There can then be no question of the actual components and quantities of medicaments which have been administered to the patient. If facilities for storage of the used mixing chambers are unavailable or too costly for particular application, a photographic or digital imaging record may easily be preserved by making an exposure of the mixing bag after preparation of the solution, and storing the image in a mechanically or electronically retrievable form. The unit dose holders may be formed with different markers, indicia, or coloring, to facilitate their identification in the record images. As a further check on the medicament contents, if sufficient computer processing capacity is available, conventional computer vision systems capable of discerning the different shapes and indicia of the unit dose holders may be employed which can identify and record the unit dose holders present in a particular mixing bag. Alternatively, bar code markings may be placed on the unit dose holders for reading by a laser scanner. The unit dose holders may be filled and quality checked by the manufacturer, where there can be certainty of successful inclusion of the proper dose in each holder.

Figure 5:
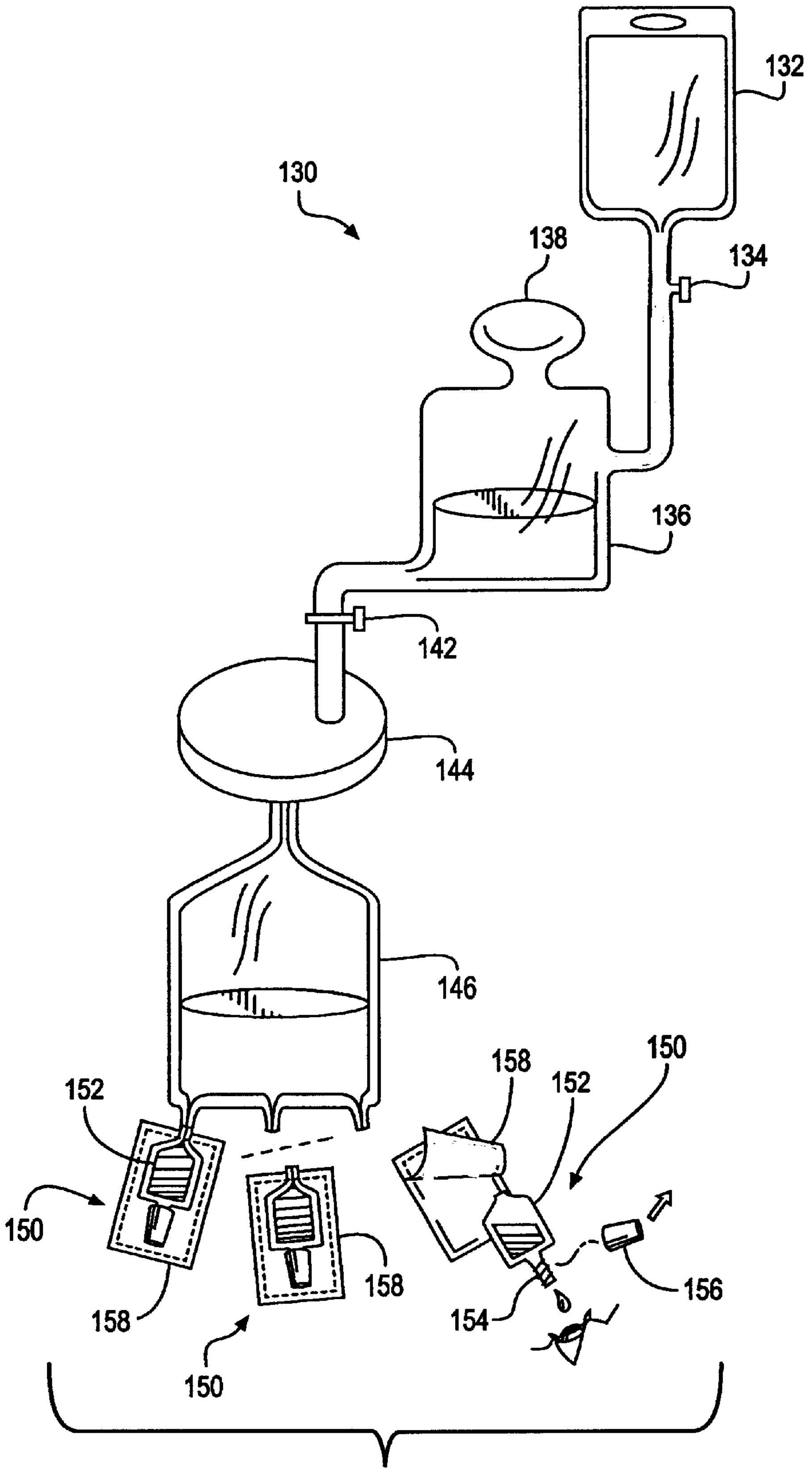
FIG. 5 is schematic view of an alternative embodiment apparatus of this invention for the preparation of ophthalmic unit doses of medicament solutions.

In addition to preparing solutions for intravenous administration, the assembly of this invention may be used to prepare individual unit dose ophthalmic solutions for application to a patient's eye, as shown in FIG. 5. The assembly 130 is similar to the assembly 22 in that it has a transparent plastic supply bag 132 prefilled with U.S.P. water and connected with a first valve 134 to a mixing bag 136. The mixing bag has an inlet 138 through which unit dose containers are introduced into a mixing chamber 138. A magnetic mixing bar 32 is disposed within the mixing bag. The mixing bag 136 is connected by a second valve 142 through a filter 144 to a pre-administration bag 146. The adding of the water and the unit dose holders 42 and the mixing and filtering of the solution is carried out just as described above. However, a plurality of ophthalmic solution containers 150 are formed to extend downwardly from the pre-administration bag 146. Each container 150 has a body 152 which holds the prescribed quantity of ophthalmic solution for a single dose, and a threaded dropper nozzle 154 which is capped with a pre-sterilized cap 156. Each container 150 and cap 156 are heat sealed within a removable plastic envelope 158. Once the solution has been drawn into the pre-administration bag 146, negative pressure is applied to the containers 150, to draw solution into the bodies 152 of the containers. Once full, a container 150 is heat sealed and severed from the pre-administration bag 146. The container 150 is then ready for later administration to a patient's eye 160 after removal of the cap 156 and the envelope 158.

It should be noted that unit dose holders of various different geometries and construction may be employed with this invention. Furthermore, the mechanism for manipulating the bags and for disposing dose holders and solution therein may be of various designs to accommodate the particular throughput and location needs of a particular application. In addition, the control of the process steps may be through any acceptable control means, such as a digital computer, a system of relays, etc.

It is understood that the invention is not limited to the particular construction and arrangement of parts herein illustrated and described, but embraces such modified forms thereof as come within the scope of the following claims.

I claim:

1. An assembly for the preparation of solutions for human administration comprising:

a first bag which retains water therein;

a mixing bag in communication with the first bag;

a first valve for controlling the admission of water from the first bag to the mixing bag;

an electric eye positioned to detect the level of the contents within the mixing bag and a controller which halts the introduction of water when the electric eye detects water reaching the desired level;

portions of the mixing bag defining an inlet opening for the introduction of medicament holders into the mixing bag;

a second bag in communication with the mixing bag;

a filter positioned between the mixing bag and the second bag; and a second valve positioned between the mixing bag and the filter, for controlling the admission of a solution to the filter.

2. The assembly of claim 1 further comprising at least one unit dose holder received within the mixing bag, the unit dose holder comprising:

a resilient air container filled with pressurized air;

a first compartment in communication with the air container;

a second compartment in communication with the first compartment, wherein portions of the second compartment define a weakened line of plastic material;

a unit dose of medicament contained in the second compartment; and at least one rupturable barrier between the air container and the first compartment, wherein external pressure applied to the air container causes the pressurized air contained therein to rupture the barrier and the weakened line of plastic material and thereby discharge the unit dose of medicament from the unit dose holder.

3. An assembly for the preparation of solutions for human administration comprising:

a first bag which retains water therein;

a mixing bag in communication with the first bag;

a first valve for controlling the admission of water from the first bag to the mixing bag;

portions of the mixing bag defining an inlet opening for the introduction of medicament holders into the mixing bag;

a second bag in communication with the mixing bag;

a filter positioned between the mixing bag and the second bag; and a second valve positioned between the mixing bag and the filter, for controlling the admission of a solution to the filter a plurality of ophthalmic dose containers extending outwardly from the second bag and in fluid-receiving communication with the second bag, each ophthalmic dose container having a body for containing solution and a dropper nozzle for discharging solution from the body; and a cap engaged with the dropper nozzle.

4. The assembly of claim 3 further comprising a plastic envelope sealed around the ophthalmic dose container and cap.

5. An apparatus for preparing solutions for administration to humans comprising:

means for supporting a mixing bag having an inlet;

means for inserting a container of a predetermined amount of medicament into the mixing bag;

means for introducing water into the mixing bag;

means for ejecting the medicament from the container;

means for mixing said ejected medicament with introduced water within the mixing bag to form a solution; and means for drawing the solution from the mixing bag through a filter into an administration bag, a computer controller responsive to radio transmitted signals to operate the means for inserting a container, the means for introducing water, the means for ejecting the medicament, the means of mixing, and the means for drawing the solution through a filter to prepare a solution in response to instructions transmitted from a remote location.

6. An apparatus for preparing solutions for administration to humans comprising:

means for supporting a mixing bag having an inlet;

means for inserting a container of a predetermined amount of medicament into the mixing bag;

means for introducing water into the mixing bag;

means for monitoring the level of water introduced into the mixing bag, and for halting the introduction of water when the level reaches a selected limit;

means for ejecting the medicament from the container;

means for mixing said ejected medicament with introduced water within the mixing bag to form a solution; and means for drawing the solution from the mixing bag through a filter into an administration bag, wherein the means for introducing water into the mixing bag comprises a valve interposed between a supply bag filled with water, the valve being subject to automatic control.

7. The apparatus of claim 6 wherein the means for introducing water into the mixing bag further comprises a positive pressure chamber enclosing the supply bag.

8. The apparatus of claim 6 wherein the means for drawing the solution from the mixing bag comprises a negative pressure chamber enclosing the administration bag.

9. The apparatus of claim 6 wherein the means for ejecting the medicament from the container comprises a mechanism which ruptures the container prior to its introduction into the mixing bag.

10. The apparatus of claim 6 wherein the means for ejecting the medicament from the container comprises a mechanism which engages the container within the bag to rupture the container and discharge the contents therefrom.

11. An apparatus for preparing solutions for administration to humans comprising:

means for supporting a mixing bag having an inlet;

means for inserting a container of a predetermined amount of medicament into the mixing bag;

means for introducing water into the mixing bag, wherein the means for introducing water into the mixing bag comprises a valve interposed between a supply bag filled with water, the valve being subject to automatic control;

means for ejecting the medicament from the container;

means for mixing said ejected medicament with introduced water within the mixing bag to form a solution; and means for drawing the solution from the mixing bag through a filter into an administration bag, wherein the means for introducing water into the mixing bag further comprises an electric eye positioned to detect the level of the contents within the mixing chamber and a controller which halts the introduction of water when the electric eye detects water reaching the desired level.

12. An apparatus for preparing solutions for administration to humans comprising:

means for supporting a mixing bag having an inlet;

means for inserting a container of a predetermined amount of medicament into the mixing bag;

means for introducing water into the mixing bag;

means for ejecting the medicament from the container;

means for mixing said ejected medicament with introduced water within the mixing bag to form a solution; and means for drawing the solution from the mixing bag through a filter into an administration bag, wherein the means for mixing comprises a ferromagnetic metal bar positioned within the mixing bag and a rotating magnetic element exterior to the mixing bag.

* * * * *